(12) United States Patent
Plaskin et al.

(10) Patent No.: US 10,869,960 B2
(45) Date of Patent: Dec. 22, 2020

(54) LOCAL DISINFECTION FOR PREFILLED DRUG DELIVERY SYSTEM

(71) Applicant: SORREL MEDICAL LTD, Netanya (IL)

(72) Inventors: Michael Plaskin, Tirat-Carmel (IL); Shahar Zidon, Kibbutz Shfaim (IL); Ori Ben-David, Tel-Aviv (IL)

(73) Assignee: SORREL MEDICAL LTD, Netanya (IL)

( * ) Notice: Subject to any disclaimer, the term of this patent is extended or adjusted under 35 U.S.C. 154(b) by 376 days.

(21) Appl. No.: 15/872,552

(22) Filed: Jan. 16, 2018

(65) Prior Publication Data

US 2019/0134295 A1    May 9, 2019

Related U.S. Application Data

(60) Provisional application No. 62/581,886, filed on Nov. 6, 2017.

(51) Int. Cl.
*A61L 2/10* (2006.01)
*A61L 2/04* (2006.01)
(Continued)

(52) U.S. Cl.
CPC .............. *A61M 5/001* (2013.01); *A61L 2/10* (2013.01); *A61L 2/24* (2013.01); *A61M 5/14212* (2013.01);
(Continued)

(58) Field of Classification Search
CPC ................................ A61M 5/001; A61L 2/10
See application file for complete search history.

(56) References Cited

U.S. PATENT DOCUMENTS 6,355,024 B1    3/2002    Small et al.
7,931,859 B2    4/2011    Mlodzinski et al.
(Continued)

FOREIGN PATENT DOCUMENTS

WO    2015/061386    4/2015
WO    2016/141082    6/2016

OTHER PUBLICATIONS

An International Search Report and a Written Opinion both dated Mar. 21, 2019, which issued during the prosecution of Applicant's PCT/IL2018/051178.
(Continued)

*Primary Examiner* — Donald R Spamer
(74) *Attorney, Agent, or Firm* — Sughrue Mion, PLLC

(57) ABSTRACT

A therapeutic substance delivery device is provided for delivering therapeutic substance to the subject. A sterile fluid path includes a needle at an upstream end of the sterile fluid path and an injection assembly at a downstream end of the sterile fluid path. The delivery device engages with a prefilled therapeutic substance reservoir, such that a disinfection chamber is defined between the sterile fluid path and the reservoir. The needle penetrates the disinfection chamber and subsequently the reservoir when the therapeutic substance delivery device and the reservoir are engaged with one another. A disinfection assembly is disposed within the delivery device and configured to disinfect the disinfection chamber prior to the needle penetrating the disinfection chamber. Control circuitry activates the disinfection assembly, terminates the activation of the disinfection assembly, and subsequently drives the needle to penetrate the disinfection chamber and subsequently the reservoir.

20 Claims, 10 Drawing Sheets

(51) Int. Cl.
  *A61L 2/16* (2006.01)
  *A61M 5/00* (2006.01)
  *A61M 5/142* (2006.01)
  *A61L 2/24* (2006.01)
  *A61M 5/14* (2006.01)
  *A61M 5/31* (2006.01)
  *A61M 5/162* (2006.01)

(52) U.S. Cl.
  CPC ...... *A61M 5/14248* (2013.01); *A61L 2202/11* (2013.01); *A61L 2202/14* (2013.01); *A61L 2202/24* (2013.01); *A61M 5/002* (2013.01); *A61M 5/1408* (2013.01); *A61M 5/162* (2013.01); *A61M 2005/3118* (2013.01)

(56) References Cited

U.S. PATENT DOCUMENTS

| | | |
|---|---|---|
| 8,431,074 B2 | 4/2013 | Neer |
| 8,540,693 B2 | 9/2013 | Arnitz et al. |
| 8,779,386 B2 | 7/2014 | Bak |
| 9,604,740 B2 | 3/2017 | Py |
| 9,901,651 B2 | 2/2018 | Finke et al. |
| 2015/0265735 A1 | 9/2015 | Ma |
| 2015/0352297 A1 | 12/2015 | Stedman et al. |
| 2017/0182242 A1 | 6/2017 | Galitz et al. |
| 2019/0111202 A1* | 4/2019 | Falkovich ................ A61L 2/10 |

OTHER PUBLICATIONS

U.S. Appl. No. 62/581,886, filed Nov. 7, 2017.

* cited by examiner

LOCAL DISINFECTION FOR PREFILLED DRUG DELIVERY SYSTEM

CROSS-REFERENCES TO RELATED APPLICATIONS

The present application claims the priority of U.S. 62/581,886 to Plaskin, filed Nov. 6, 2017, entitled, "Local disinfection for prefilled drug delivery system," which is incorporated herein by reference.

FIELD OF THE INVENTION

The present invention relates generally to delivery of a therapeutic substance to a subject, and more specifically to wearable drug delivery devices utilizing prefilled therapeutic substance reservoirs.

BACKGROUND

Pumps are often used in the medical industry for delivering therapeutic substances, e.g., drugs, to subjects. Therapeutic substances such as saline solution, insulin, antibiotics, chemotherapy drugs, and biosimilar drugs may all be delivered to a subject with medical pumps. Some medical pumps utilize therapeutic substance reservoirs that are prefilled by a pharmaceutical company. The medical pumps may be manufactured in a controlled environment and subsequently sterilized, and the therapeutic substance reservoirs may be prefilled in a sterile environment. When engaging a medical pump with a prefilled therapeutic substance reservoir, bacteria or viruses may be introduced into the engagement site.

SUMMARY OF THE INVENTION

Apparatus, such as for example a wearable medical patch pump, is provided for use with a prefilled therapeutic substance reservoir such that after engaging the pump with the reservoir, the engagement site between the pump and the reservoir is disinfected prior to fluid communication between the pump and the reservoir being established. In accordance with some applications of the present invention, the apparatus includes a therapeutic substance delivery device, inside of which is a sterile fluid path for delivering therapeutic substance to a subject. At an upstream end of the sterile fluid path is a needle for penetrating the reservoir and at a downstream end of the sterile fluid path is an injection assembly for penetrating the subject's body. When the therapeutic substance delivery device is engaged with the prefilled therapeutic substance reservoir, a disinfection chamber is defined between the sterile fluid path and the reservoir. A disinfection assembly is disposed within the therapeutic substance delivery device and is configured to disinfect the disinfection chamber. Control circuitry activates the disinfection assembly, terminates the activation of the disinfection assembly, and then drives the needle to penetrate the disinfection chamber and subsequently the reservoir. Thereby fluid communication between the reservoir and the sterile fluid path is established with reduced risk of potentially harmful bacteria coming in to contact with the therapeutic substance.

There is therefore provided, in accordance with some applications of the present invention, apparatus for delivering a therapeutic substance to a subject, the apparatus including:

a therapeutic substance delivery device:

(a) including a sterile fluid path for delivering the therapeutic substance to the subject, the sterile fluid path including a needle at an upstream end of the sterile fluid path and an injection assembly at a downstream end of the sterile fluid path, and (b) configured to engage with a prefilled therapeutic substance reservoir, such that when the therapeutic substance delivery device and the reservoir are engaged with one another a disinfection chamber is defined between the sterile fluid path and the reservoir, the needle being configured to penetrate the disinfection chamber and subsequently the reservoir when the therapeutic substance delivery device and the reservoir are engaged with one another, such that fluid communication is established between the reservoir and the sterile fluid path;

a disinfection assembly disposed within the therapeutic substance delivery device and configured to disinfect the disinfection chamber prior to the needle penetrating the disinfection chamber; and control circuitry configured to (a) activate the disinfection assembly, (b) terminate the activation of the disinfection assembly, and subsequently (c) drive the needle to penetrate the disinfection chamber and subsequently the reservoir.

For some applications, the control circuitry is configured to terminate the activation of the disinfection assembly within 5 minutes after activating the disinfection assembly.

For some applications, the control circuitry is configured to drive the needle to penetrate the disinfection chamber within 10 seconds after terminating the activation of the disinfection assembly.

For some applications, a surface area of the disinfection chamber is 1-400 mm2.

For some applications, the disinfection assembly includes an ultraviolet radiation source that is configured to emit ultraviolet radiation through a wall of the disinfection chamber.

For some applications, the ultraviolet radiation source is configured to emit the ultraviolet radiation at a power level of less than 200 mW.

For some applications, the ultraviolet radiation source is configured to emit the ultraviolet radiation at a wavelength of 100-400 nm.

For some applications, the ultraviolet radiation source is configured to emit the ultraviolet radiation at a plurality of wavelengths.

For some applications, the ultraviolet radiation source includes an ultraviolet light emitting diode.

For some applications, at least one surface of the disinfection chamber is a reflective surface configured to reflect the ultraviolet radiation.

For some applications, the reflective surface is configured to reflect at least 10% of the ultraviolet radiation.

For some applications, the disinfection assembly includes a heat source and the control circuitry is configured to activate the heat source to heat the disinfection chamber.

For some applications, the control circuitry is configured to activate the heat source to heat the disinfection chamber to a temperature of 40-300 degrees Celsius.

For some applications, the disinfection assembly includes a disinfectant fluid assembly including a disinfectant fluid reservoir containing disinfectant fluid, and the control circuitry is configured to activate the disinfectant fluid assembly to release the disinfectant fluid from the disinfectant fluid reservoir into the disinfection chamber.

For some applications, the control circuitry is further configured to activate the therapeutic substance delivery device to deliver the therapeutic substance to the subject.

For some applications, the apparatus further includes the prefilled therapeutic substance reservoir, and the apparatus is packaged for commercial sale with the therapeutic substance delivery device and the reservoir engaged with one another.

For some applications, the apparatus further includes the prefilled therapeutic substance reservoir, and the apparatus is packaged for commercial sale with the therapeutic substance delivery device and the reservoir not engaged with one another.

For some applications, the apparatus is packaged for commercial sale without the prefilled therapeutic substance reservoir.

For some applications, the sterile fluid path is a first sterile fluid path and the needle is a first needle, the therapeutic substance delivery device:
 (a) further including a second sterile fluid path, the second sterile fluid path including a second needle at an upstream end of the second sterile fluid path and the injection assembly at a downstream end of the second fluid path,
 (b) further configured to engage with a second prefilled therapeutic substance reservoir, such that when the first and second reservoirs are engaged with the therapeutic substance delivery device first and second disinfection chambers are defined respectively (i) between the first sterile fluid path and the first reservoir, and (ii) between the second sterile fluid path and the second reservoir,
 (c) further including a first sterile fluid path valve disposed between the first needle and the injection assembly and configured to control fluid communication between the first reservoir and the injection assembly, and
 (d) further including a second sterile fluid path valve disposed between the second needle and the injection assembly and configured to control fluid communication between the second reservoir and the injection assembly,
the first and second needles being configured to penetrate the first and second disinfection chambers respectively and subsequently the first and second reservoirs respectively when the therapeutic substance delivery device is engaged with the first and second reservoirs, such that a first fluid communication is established between the first sterile fluid path and the first reservoir and a second fluid communication is established between the second sterile fluid path and the second reservoir, and
the disinfection assembly being configured to (a) disinfect the first disinfection chamber prior to the first needle penetrating the first disinfection chamber, and (b) disinfect the second disinfection chamber prior to the second needle penetrating the second disinfection chamber.

For some applications, the disinfection assembly is a first disinfection assembly configured to disinfect the first disinfection chamber, the apparatus further includes a second disinfection assembly configured to disinfect the second disinfection chamber, and the control circuitry is configured to activate the first and second disinfection assemblies.

For some applications:
 (a) the needle is a first needle and the sterile fluid path further includes a second needle at the upstream end of the sterile fluid path,
 (b) when the therapeutic substance delivery device and the reservoir are engaged with one another the first and second needles are configured to penetrate the disinfection chamber and subsequently the reservoir such that fluid communication is established between the reservoir and the sterile fluid path via the first and second needles, and
 (c) the control circuitry is configured to drive the first and second needles to penetrate the disinfection chamber, within 10 seconds after terminating the activation of the disinfection assembly.

There is further provided, in accordance with some applications of the present invention, a method including:
 engaging a prefilled therapeutic substance reservoir with a therapeutic substance delivery device, such that a disinfection chamber is defined between the reservoir and a sterile fluid path disposed within the therapeutic substance delivery device, the sterile fluid path including a needle at an upstream end of the sterile fluid path and an injection assembly at a downstream end of the sterile fluid path;
 disinfecting the disinfection chamber; and
 subsequently, penetrating the disinfection chamber and then the reservoir with the needle.

For some applications, disinfecting the disinfection chamber includes activating a disinfection assembly and subsequently terminating the activation of the disinfection assembly, and wherein penetrating the disinfection chamber includes penetrating the disinfection chamber within 10 seconds after terminating the activation of the disinfecting chamber.

For some applications, disinfecting the disinfection chamber includes activating a disinfection assembly and terminating activation of the disinfection assembly within 5 minutes after activating the disinfection assembly.

For some applications, disinfecting the disinfection chamber includes irradiating the disinfection chamber with ultraviolet radiation.

For some applications, irradiating the disinfection chamber includes irradiating the disinfection chamber with ultraviolet radiation at a power level of less than 200 mW.

For some applications, irradiating the disinfection chamber includes irradiating the disinfection chamber with ultraviolet radiation at a wavelength of 100-400 nm.

For some applications, irradiating the disinfection chamber with the ultraviolet radiation includes irradiating the disinfection chamber with ultraviolet radiation at a plurality of wavelengths.

For some applications, irradiating the disinfection chamber includes irradiating the disinfection chamber with ultraviolet light using an ultraviolet light emitting diode.

For some applications, disinfecting the disinfection chamber includes heating the disinfection chamber.

For some applications, heating the disinfection chamber includes heating the disinfection chamber to a temperature of 40-300 degrees Celsius.

For some applications, disinfecting the disinfection chamber includes releasing a disinfectant fluid into the disinfection chamber.

The present invention will be more fully understood from the following detailed description of applications thereof, taken together with the drawings, in which:

DETAILED DESCRIPTION

Figure 1A:
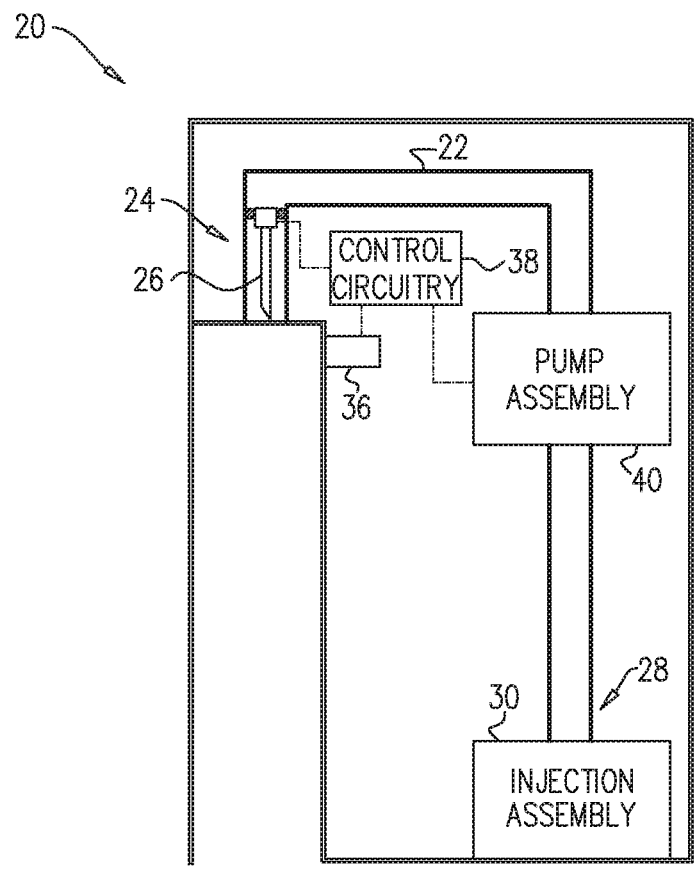
FIG. 1A is a schematic illustration of a therapeutic substance delivery device that includes a disinfection assembly and is configured to engage with a prefilled therapeutic substance reservoir, the reservoir being shown outside the therapeutic substance delivery device, in accordance with some applications of the present invention.
Figure 1A:
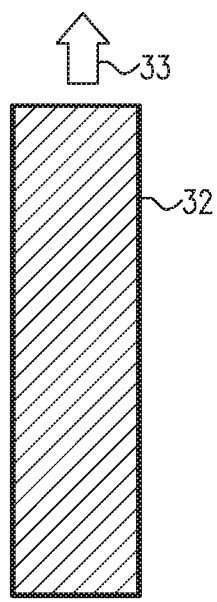
Figure 1B:
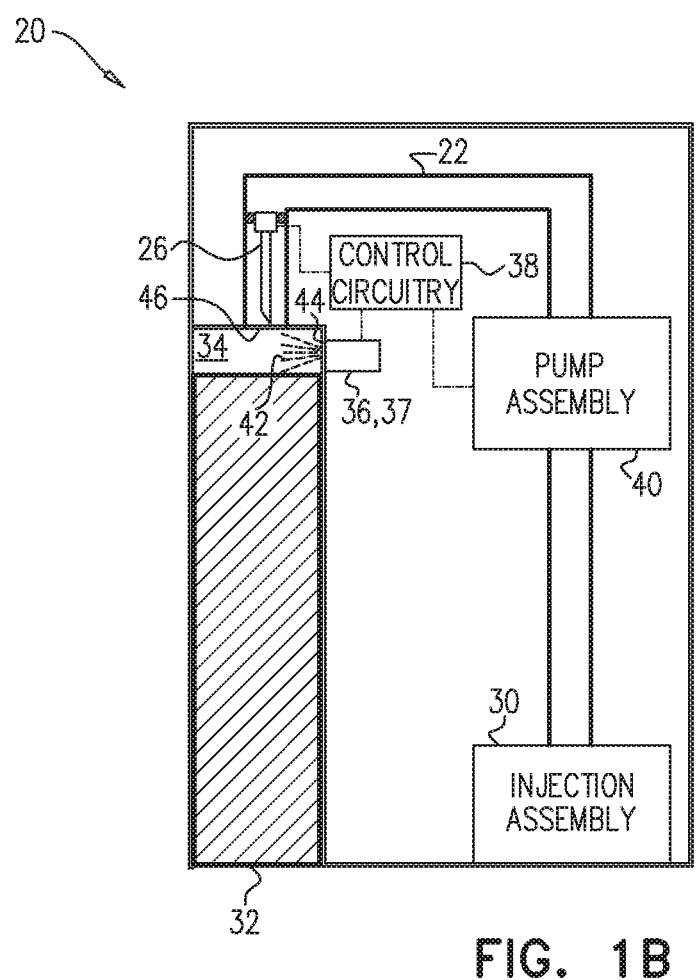
FIG. 1B is a schematic illustration of the therapeutic substance delivery device of FIG. 1A with the prefilled therapeutic substance reservoir shown engaged with the therapeutic substance delivery device, in accordance with some applications of the present invention.
Figure 1C:
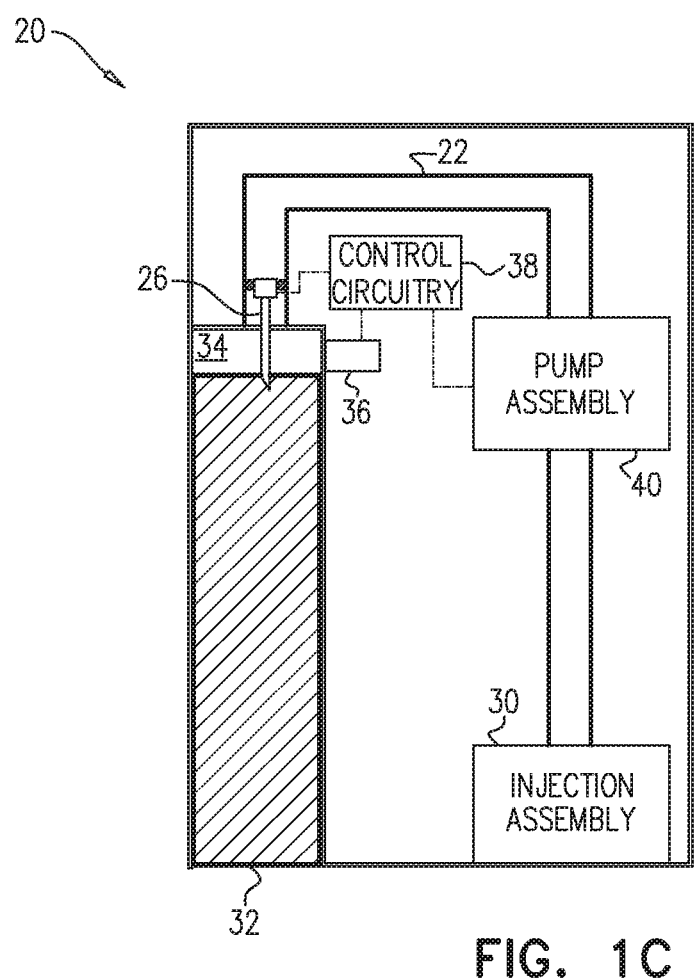
FIG. 1C is a schematic illustration of the therapeutic substance delivery device of FIGS. 1A-B, showing establishment of fluid communication by penetration of the reservoir with a needle, in accordance with some applications of the present invention.

Reference is now made to FIGS. 1A-C, which are schematic illustrations of a therapeutic substance delivery device 20 configured to engage with a prefilled therapeutic substance reservoir 32, in accordance with some applications of the present invention. Within therapeutic substance delivery device 20 is a sterile fluid path 22 for delivering therapeutic substance to a subject. Sterile fluid path 22 has a needle 26 at an upstream end 24 of sterile fluid path 22, and an injection assembly 30 at a downstream end 28 of sterile fluid path 22. Therapeutic substance delivery device 20 and prefilled therapeutic substance reservoir 32 are configured to engage with one another, such as shown by arrow 33 in FIG. 1A, e.g., reservoir 32 is configured to be inserted into therapeutic substance delivery device 20. When therapeutic substance delivery device 20 and reservoir 32 are engaged with one another, such as is shown in FIG. 1B, a sealed disinfection chamber 34 is defined between sterile fluid path 22 and reservoir 32. While therapeutic substance delivery device 20 and reservoir 32 are typically sterile, disinfection chamber 34 is (a) initially non-sterile, and (b) typically sealed from further bacteria or virus penetration. Needle 26 is driven to penetrate disinfection chamber 34 and subsequently reservoir 32 when therapeutic substance delivery device 20 and reservoir 32 are engaged with one another, such that fluid communication is established between reservoir 32 and sterile fluid path 22, such as is shown in FIG. 1C.

Disposed within therapeutic substance delivery device 20 is a disinfection assembly 36 that disinfects disinfection chamber 34 prior to needle 26 penetrating disinfection chamber 34. Control circuitry 38 activates disinfection assembly 36, terminates the activation of disinfection assembly 36, and then drives needle 26 to penetrate disinfection chamber 34 and subsequently reservoir 32. Once fluid communication is established between reservoir 32 and sterile fluid path 22, control circuitry 38 drives a pump assembly 40 to draw therapeutic substance from reservoir 32 and deliver it to the subject via injection assembly 30.

Typically, in order to decrease the amount of time spent disinfecting, disinfection chamber 34 is small. For example, a total surface area of disinfection chamber 34 may be at least 1 mm2 and/or less than 400 mm2. Disinfection can therefore typically occur within 5 minutes, e.g., within 10 seconds. Control circuitry is typically configured to terminate the activation of disinfection assembly 36 within 5 minutes, e.g., within 10 seconds, after activating disinfection assembly 36.

Local disinfection of the engagement site between reservoir 32 and therapeutic substance delivery device 20 from inside the delivery device allows for engagement of reservoir 32 and therapeutic substance delivery device 20 to occur substantially prior to therapeutic substance delivery device 20 being used to deliver the therapeutic substance to a subject, while disinfection of the engagement site may not occur until moments before delivery of the therapeutic substance. For example, prefilled therapeutic substance reservoir 32 may be inserted into therapeutic substance delivery device 20 up to 3 years prior to therapeutic substance delivery device 20 being used for delivery of a therapeutic substance. Once attached to a subject, a user control may be used to activate control circuitry 38. In response to activation by the user control, control circuitry 38 (a) activates disinfection assembly 36 such that disinfection chamber 34 is disinfected, (b) terminates the activation of disinfection assembly 36 within 5 minutes after activating disinfection assembly 36, and (c) drives needle 26 to penetrate disinfection chamber 34 within 10 seconds after terminating the activation of disinfection assembly 36.

Additionally, local disinfection of the engagement site that (a) occurs inside the delivery device after the engagement, and (b) is activated by control circuitry 38, reduces a risk of potentially harmful bacteria or viruses coming in to contact with the therapeutic substance in a way that is automated and integrated into therapeutic substance delivery device 20. Typically, reservoir 32 does not have to be disinfected prior to engagement with therapeutic substance delivery device 20, e.g., by swabbing reservoir 32 with alcohol, nor does engagement of the reservoir and the therapeutic substance delivery device have to occur while the reservoir and the fluid path are contained within a sterile environment.

For some applications, the apparatus may be packaged for commercial sale with therapeutic substance delivery device 20 and prefilled therapeutic substance reservoir 32 already engaged with one another and configured for use within 3 years. Alternatively, therapeutic substance delivery device 20 may be packaged for commercial sale along with prefilled therapeutic substance reservoir 32, but without therapeutic substance delivery device 20 and reservoir 32 being already engaged. Alternatively, therapeutic substance delivery device 20 may be packaged for commercial sale on its own, without prefilled therapeutic substance reservoir 32.

Reference is now made to FIG. 1B. For some applications, disinfection assembly 36 is an ultraviolet radiation source 37, e.g., an ultraviolet light emitting diode, that is configured to irradiate disinfection chamber 34 by emitting ultraviolet radiation 42 through a wall 44 of disinfection chamber 34. Ultraviolet radiation source 37 is typically configured to emit ultraviolet radiation 42 at a wavelength of 100-400 nm. Ultraviolet radiation source 37 may be configured to emit ultraviolet radiation 42 at a plurality of wavelengths.

For some applications, at least one surface of disinfection chamber 34, such as surface 46, is a reflective surface configured to reflect ultraviolet radiation 42. For example, surface 46 may be configured to reflect at least 10% of ultraviolet radiation 42. Surface 46 being reflective and disinfection chamber 34 being small, as described hereinabove, may independently and/or in combination allow for the disinfection assembly 36 to operate on low power. Typically, ultraviolet radiation source 37 is configured to emit ultraviolet radiation 42 at a power level of less than 200 mW.

For some applications, disinfection assembly 36 is a heat source. When activated by control circuitry 38, the heat source disinfects disinfection chamber 34 by heating disinfection chamber 34 to a temperature of 40-300 degrees Celsius. Alternatively, for some applications, disinfection assembly 36 may be a disinfectant fluid assembly having a disinfectant fluid reservoir that contains disinfectant fluid. When activated by control circuitry 38, the disinfectant fluid assembly releases the disinfectant fluid, e.g., sprays, the disinfectant fluid from the disinfectant fluid reservoir into disinfection chamber 34.

Figure 2A:
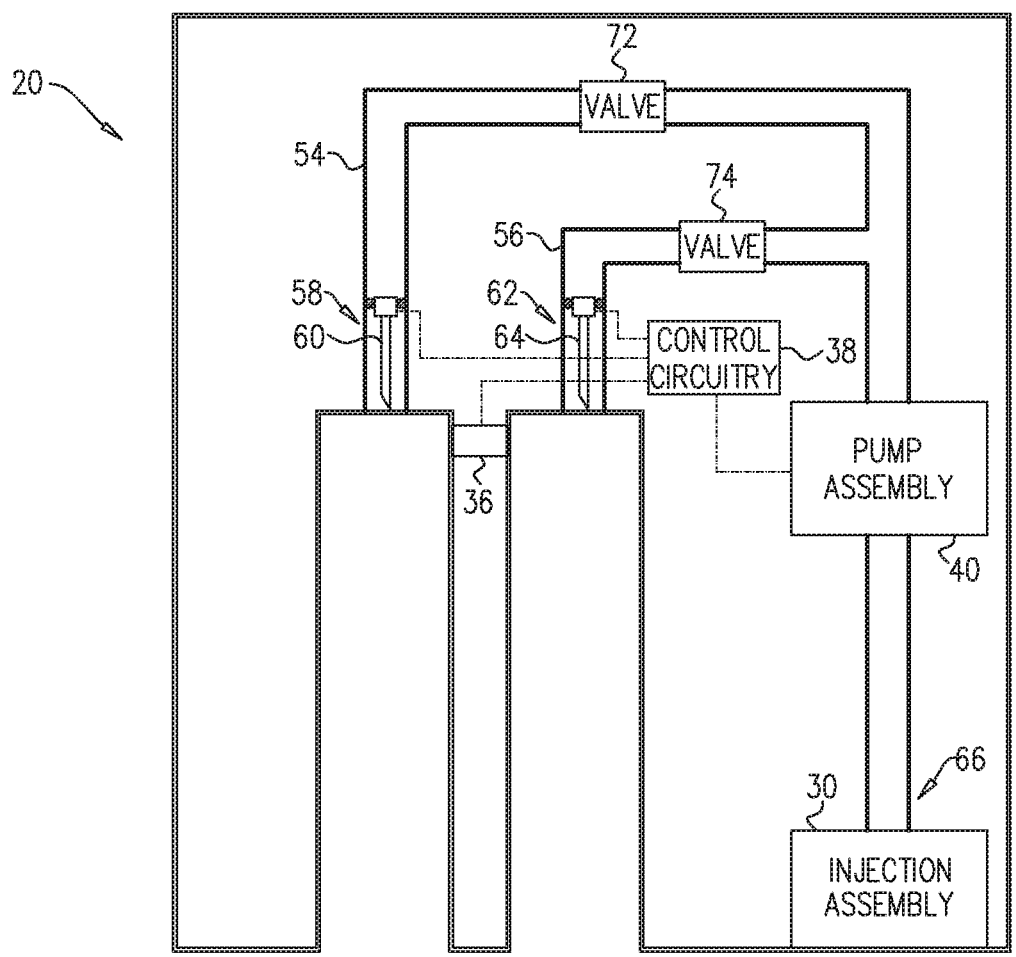
FIG. 2A is a schematic illustration of a therapeutic substance delivery device that includes a disinfection assembly and is configured to engage with two prefilled therapeutic substance reservoirs, the reservoirs being shown outside the therapeutic substance delivery device, in accordance with some applications of the present invention.
Figure 2B:
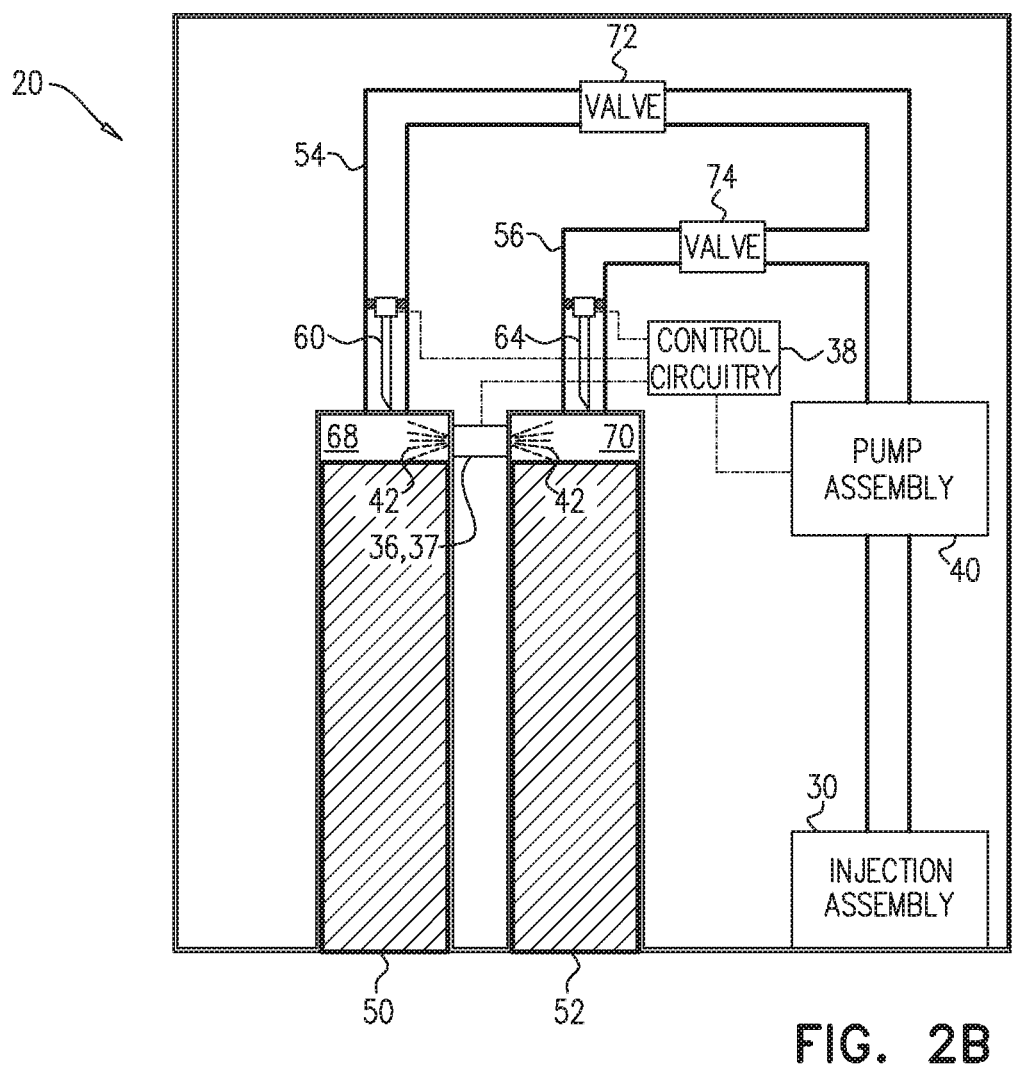
FIG. 2B is a schematic illustration of the therapeutic substance delivery device of FIG. 2A with the prefilled therapeutic substance reservoirs shown engaged with the therapeutic substance delivery device, in accordance with some applications of the present invention.
Figure 2C:
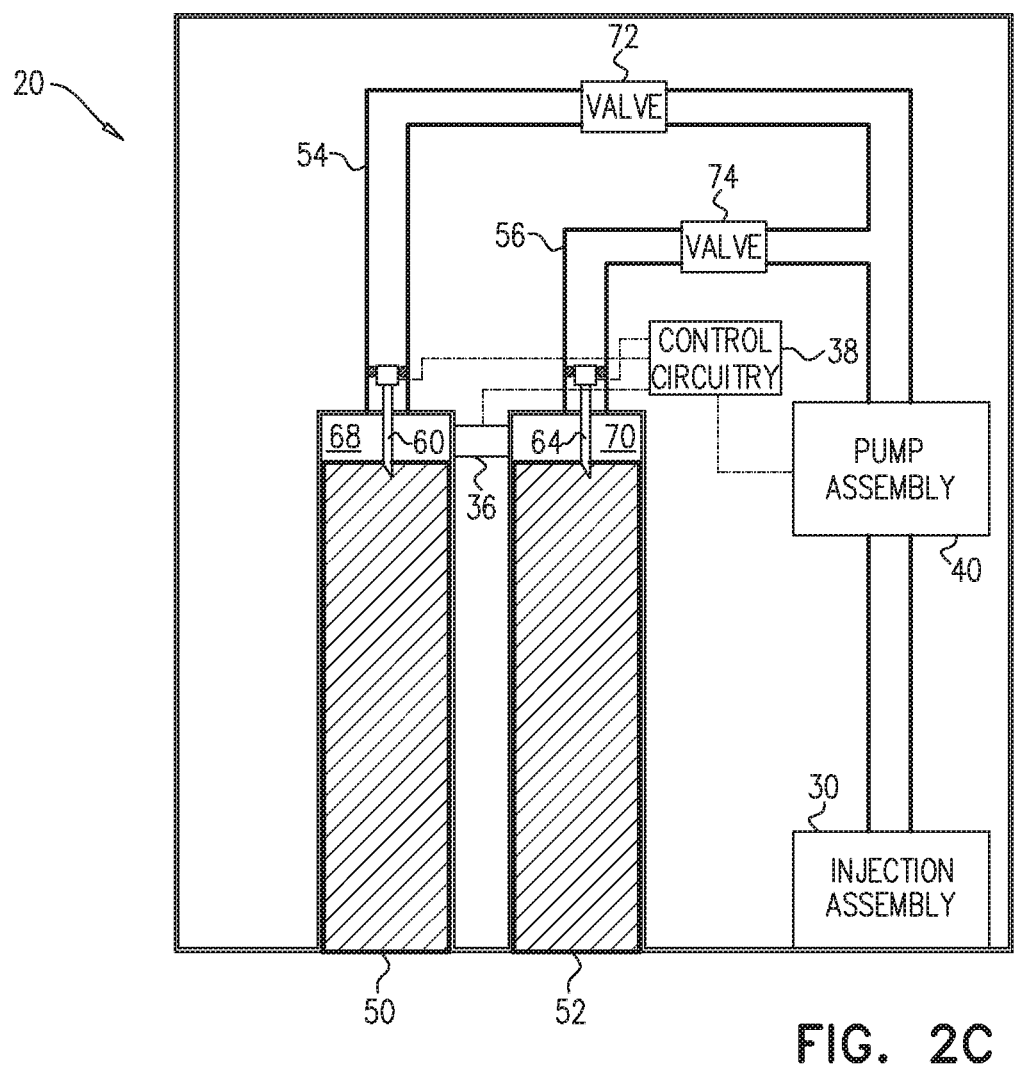
FIG. 2C is a schematic illustration of the therapeutic substance delivery device of FIGS. 2A-B showing establishment of fluid communication by penetration of the reservoirs with respective needles, in accordance with some applications of the present invention.

Reference is now made to FIGS. 2A-C, which are schematic illustrations of therapeutic substance delivery device 20 configured to engage with a first prefilled therapeutic substance reservoir 50 and a second prefilled therapeutic substance reservoir 52, in accordance with some applications of the present invention. For some applications, therapeutic substance delivery device 20 has a first sterile fluid path 54 and a second sterile fluid path 56. At an upstream end 58 of first sterile fluid path is a first needle 60, and at an upstream end 62 of second sterile fluid path 56 is a second needle 64. First sterile fluid path 54 and second sterile fluid path 56 share a common downstream end 66, at which is disposed injection assembly 30. When first prefilled therapeutic substance reservoir 50 and second prefilled therapeutic substance reservoir 52 are engaged with therapeutic substance delivery device 20, such as is shown in FIG. 2B, (a) a first disinfection chamber 68 is defined between first sterile fluid path 54 and first reservoir 50, and (b) a second disinfection chamber 70 is defined between second sterile fluid path 56 and second reservoir 52.

First needle 60 and second needle 64 are driven by control circuitry 38 to penetrate first disinfection chamber 68 and second disinfection chamber 70 respectively, and subsequently first reservoir 50 and second reservoir 52 respectively, such as is shown in FIG. 2C. Thereby a first fluid communication is established between first sterile fluid path 54 and first reservoir 50, and a second fluid communication is established between second sterile fluid path 56 and second reservoir 52. When activated by control circuitry 38, disinfection assembly 36, e.g., ultraviolet radiation source 37, (a) disinfects first disinfection chamber 68 prior to first needle 60 penetrating first disinfection chamber 68, and (b) disinfects second disinfection chamber 70 prior to second needle 64 penetrating second disinfection chamber 70. For example, ultraviolet radiation source 37 may emit ultraviolet radiation 42 through respective walls of first disinfection chamber 68 and second disinfection chamber 70. Within 5 minutes after activation, control circuitry 38 terminates the activation of disinfection assembly 36, and subsequently drives first needle 60 and second needle 64 to respectively penetrate first disinfection chamber 68 and second disinfection chamber 70 within 10 seconds after terminating the activation of disinfection assembly 36.

Typically, two valves are used to control fluid communication between the respective reservoirs and injection assembly 30. For example, a first sterile fluid path valve 72 may be disposed between first needle 60 and injection assembly 30 to control fluid communication between first reservoir 50 and injection assembly 30, and a second sterile fluid path valve 74 may be disposed between second needle 64 and injection assembly 30 to control fluid communication between second reservoir 52 and injection assembly 30.

Figure 2D:
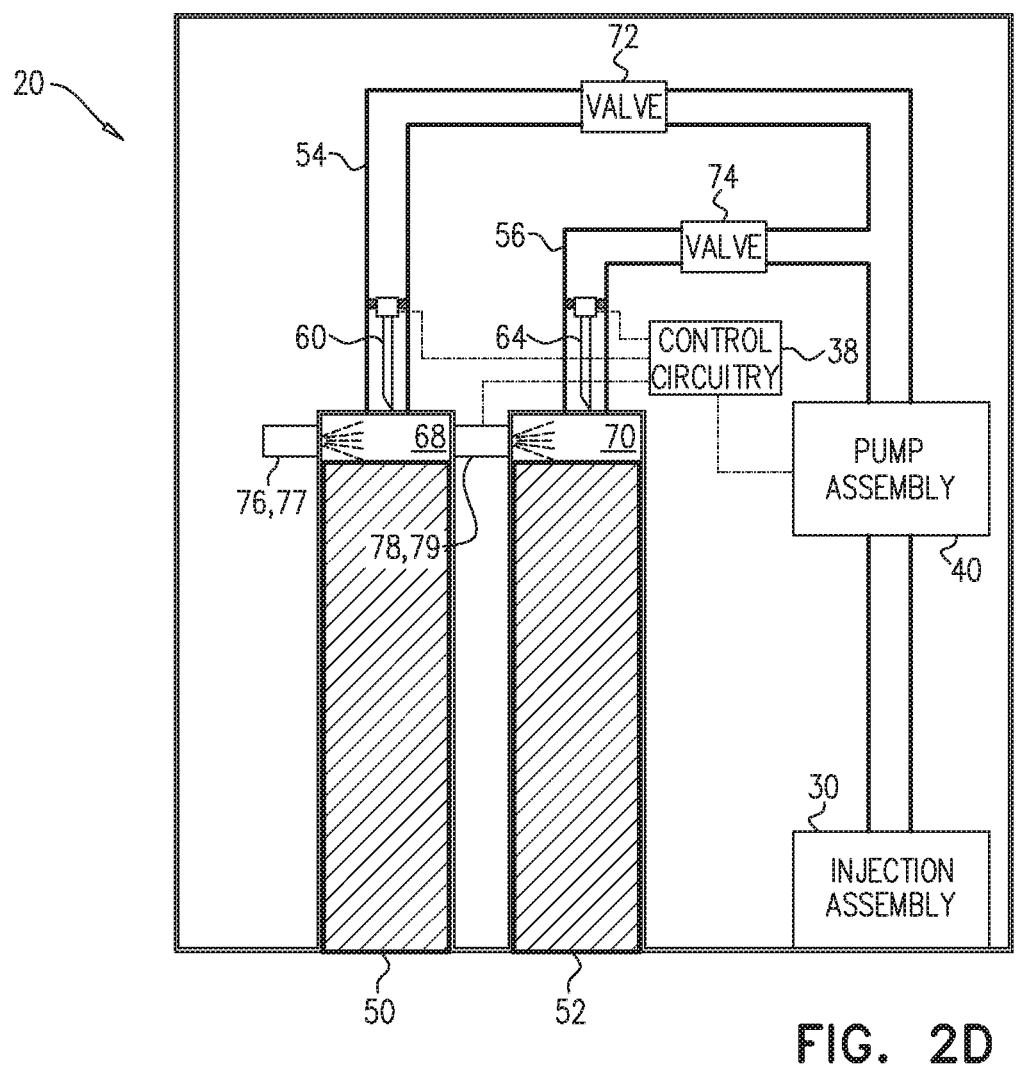
FIG. 2D is a schematic illustration of a therapeutic substance delivery device that includes two disinfection assemblies and is configured to engage with two prefilled therapeutic substance reservoirs, the reservoirs being shown engaged with the therapeutic substance delivery device, in accordance with some applications of the present invention.

Reference is now made to FIG. 2D, which is a schematic illustration of therapeutic substance delivery device 20 with two disinfection assemblies. For some applications, instead of using one disinfection assembly to disinfect both disinfection chambers, a first disinfection assembly 76, e.g., a first ultraviolet radiation source 77, disinfects first disinfection chamber 68, and a second disinfection assembly 78, e.g., a second ultraviolet radiation source 79, disinfects second disinfection chamber 70. Control circuitry 38 may activate the first and second disinfection assemblies simultaneously or independently of each other. When first disinfection assembly 76 and second disinfection assembly 78 are activated independently, control circuitry 38 (a) drives first needle 60 to penetrate first disinfection chamber 68 within 10 seconds after terminating the activation of first disinfection assembly 76, and (b) drives second needle 64 to penetrate second disinfection chamber 70 within 10 seconds after terminating the activation of second disinfection assembly 78. All features of disinfection assembly 36 described hereinabove with reference to FIGS. 1A-C and FIGS. 2A-C may apply to first disinfection assembly 76 and second disinfection assembly 78.

Figure 3A:
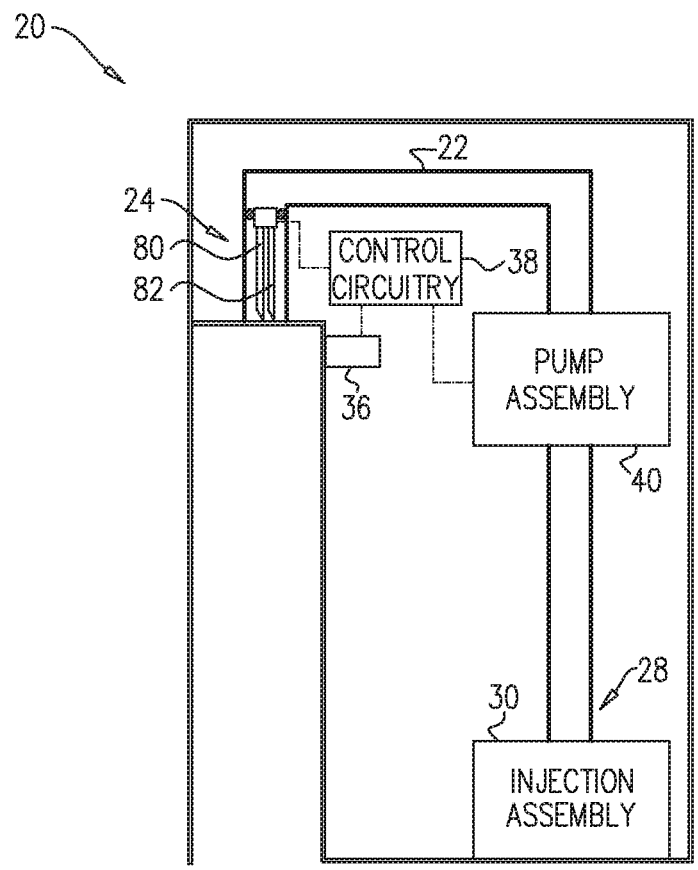
FIG. 3A is a schematic illustration of a therapeutic substance delivery device that includes a disinfection assembly and two needles, and is configured to engage with a prefilled therapeutic substance reservoir, the reservoir being shown outside the therapeutic substance delivery device, in accordance with some applications of the present invention.
Figure 3A:
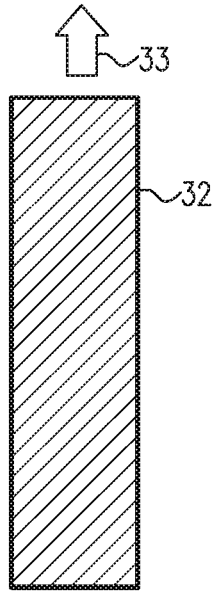
Figure 3B:
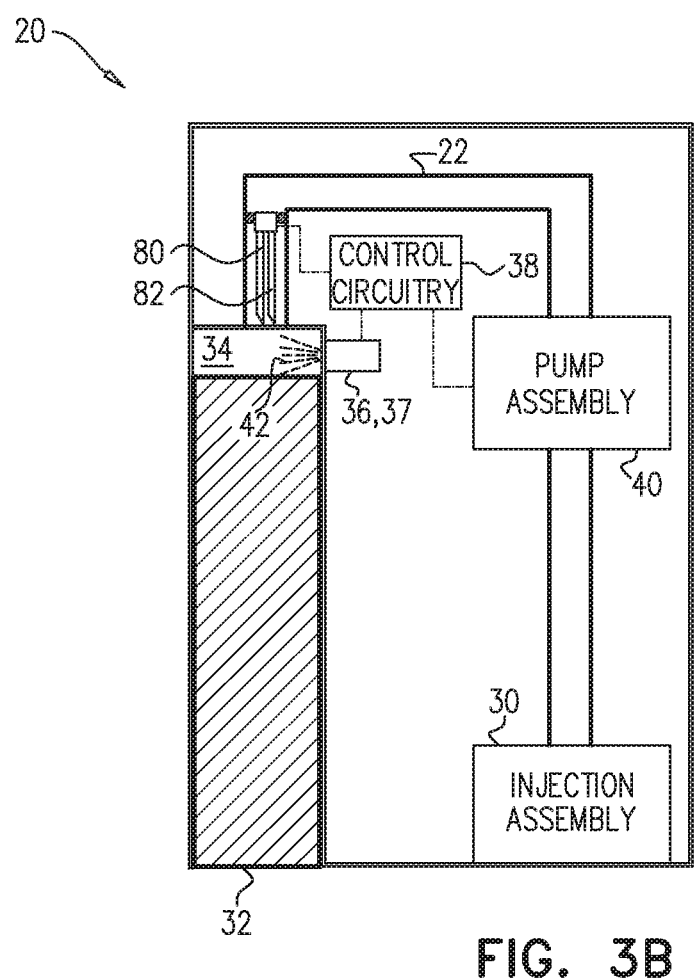
FIG. 3B is a schematic illustration of the therapeutic substance delivery device of FIG. 3A with the prefilled therapeutic substance reservoir engaged with the therapeutic substance delivery device, in accordance with some applications of the present invention.
Figure 3C:
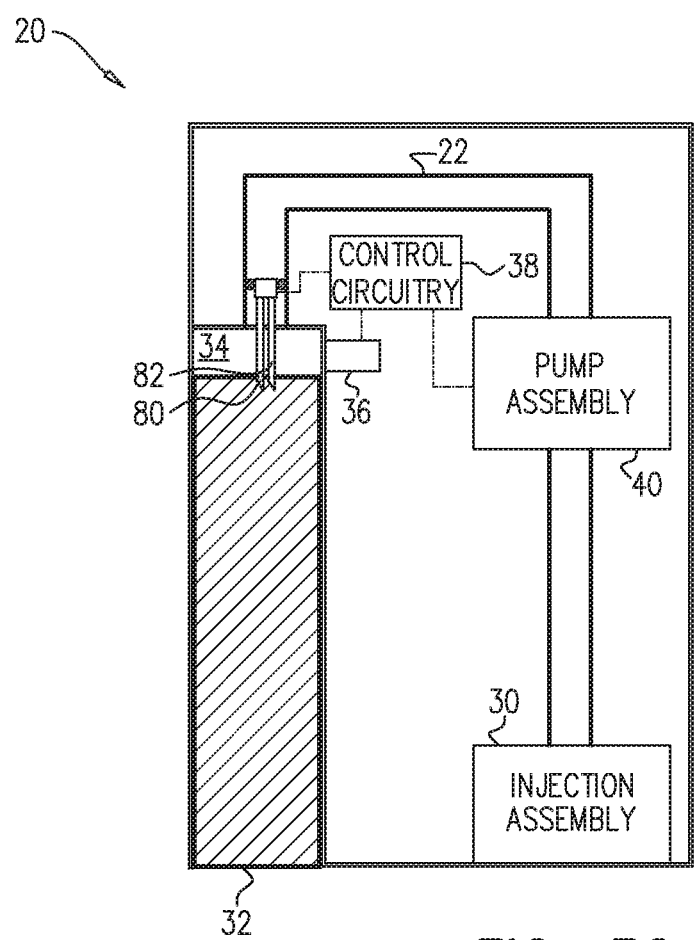
FIG. 3C is a schematic illustration of the therapeutic substance delivery device of FIGS. 3A-B, showing establishment of fluid communication by penetration of the reservoir with the two needles, in accordance with some applications of the present invention.

Reference is now made to FIGS. 3A-C, which are schematic illustrations of therapeutic substance delivery device 20 configured to engage with prefilled therapeutic substance reservoir 32, in accordance with some applications of the present invention. For some applications, to increase the rate of flow of the therapeutic substance, more than one needle may be used to establish fluid communication between reservoir 32 and sterile fluid path 22. For example, a first needle 80 and a second needle 82 may be disposed at upstream end 24 of sterile fluid path 22. Control circuitry 38 activates disinfection assembly 36, e.g., ultraviolet radiation source 37, to disinfect disinfection chamber (FIG. 3B), terminates the activation of disinfection assembly 36 within 5 minutes, and subsequently drives first needle 80 and second needle 82 to penetrate disinfection chamber 34 and subsequently reservoir 32 (FIG. 3C) within 10 seconds after terminating the activation of disinfection assembly 36. Fluid communication is thereby established via first needle 80 and second needle 82.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for delivering a therapeutic substance to a subject, the apparatus comprising:
   a therapeutic substance delivery device:
   (a) comprising a sterile fluid path for delivering the therapeutic substance to the subject, the sterile fluid path comprising a needle at an upstream end of the sterile fluid path and an injection assembly at a downstream end of the sterile fluid path, and
   (b) configured to engage with a prefilled therapeutic substance reservoir, such that when the therapeutic substance delivery device and the reservoir are engaged with one another a disinfection chamber is defined between the sterile fluid path and the reservoir, the needle being configured to penetrate the disinfection chamber and subsequently the reservoir when the therapeutic substance delivery device and the reservoir are engaged with one another, such that fluid communication is established between the reservoir and the sterile fluid path;
   a disinfection assembly disposed within the therapeutic substance delivery device and configured to disinfect the disinfection chamber prior to the needle penetrating the disinfection chamber; and
   control circuitry configured to (a) activate the disinfection assembly, (b) terminate the activation of the disinfection assembly, and subsequently (c) drive the needle to penetrate the disinfection chamber and subsequently the reservoir.

2. The apparatus according to claim 1, wherein the control circuitry is configured to terminate the activation of the disinfection assembly within 5 minutes after activating the disinfection assembly.

3. The apparatus according to claim 2, wherein the control circuitry is configured to drive the needle to penetrate the disinfection chamber within 10 seconds after terminating the activation of the disinfection assembly.

4. The apparatus according to claim 1, wherein a surface area of the disinfection chamber is 1-400 mm2.

5. The apparatus according to claim 1, wherein the control circuitry is further configured to activate the therapeutic substance delivery device to deliver the therapeutic substance to the subject.

6. The apparatus according to claim 1, further comprising the prefilled therapeutic substance reservoir, and wherein the apparatus is packaged for commercial sale with the therapeutic substance delivery device and the reservoir engaged with one another.

7. The apparatus according to claim 1, further comprising the prefilled therapeutic substance reservoir, and wherein the apparatus is packaged for commercial sale with the therapeutic substance delivery device and the reservoir not engaged with one another.

8. The apparatus according to claim 1, wherein the sterile fluid path is a first sterile fluid path and the needle is a first needle, the therapeutic substance delivery device:
   (a) further comprising a second sterile fluid path, the second sterile fluid path comprising a second needle at an upstream end of the second sterile fluid path and the injection assembly at a downstream end of the second fluid path,
   (b) further configured to engage with a second prefilled therapeutic substance reservoir, such that when the first and second reservoirs are engaged with the therapeutic substance delivery device first and second disinfection chambers are defined respectively (i) between the first sterile fluid path and the first reservoir, and (ii) between the second sterile fluid path and the second reservoir,
   (c) further comprising a first sterile fluid path valve disposed between the first needle and the injection assembly and configured to control fluid communication between the first reservoir and the injection assembly, and
   (d) further comprising a second sterile fluid path valve disposed between the second needle and the injection assembly and configured to control fluid communication between the second reservoir and the injection assembly,
   wherein the first and second needles are configured to penetrate the first and second disinfection chambers respectively and subsequently the first and second reservoirs respectively when the therapeutic substance delivery device is engaged with the first and second reservoirs, such that a first fluid communication is established between the first sterile fluid path and the first reservoir and a second fluid communication is established between the second sterile fluid path and the second reservoir, and
   wherein the disinfection assembly is configured to (a) disinfect the first disinfection chamber prior to the first needle penetrating the first disinfection chamber, and (b) disinfect the second disinfection chamber prior to the second needle penetrating the second disinfection chamber.

9. The apparatus according to claim 1, wherein:
   (a) the needle is a first needle and the sterile fluid path further comprises a second needle at the upstream end of the sterile fluid path,
   (b) when the therapeutic substance delivery device and the reservoir are engaged with one another the first and second needles are configured to penetrate the disinfection chamber and subsequently the reservoir such that fluid communication is established between the reservoir and the sterile fluid path via the first and second needles, and
   (c) the control circuitry is configured to drive the first and second needles to penetrate the disinfection chamber, within 10 seconds after terminating the activation of the disinfection assembly.

10. The apparatus according to claim 1, wherein the disinfection assembly comprises an ultraviolet radiation source.

11. The apparatus according to claim 10, wherein the ultraviolet radiation source is configured to emit ultraviolet radiation at a power level of less than 200 mW.

12. The apparatus according to claim 10, wherein the ultraviolet radiation source is configured to emit the ultraviolet radiation at a wavelength of 100-400 nm.

13. The apparatus according to claim 10, wherein the ultraviolet radiation source is configured to emit the ultraviolet radiation at a plurality of wavelengths.

14. The apparatus according to claim 10, wherein the ultraviolet radiation source comprises an ultraviolet light emitting diode.

15. The apparatus according to claim 10, wherein at least one surface of the disinfection chamber is a reflective surface configured to reflect ultraviolet radiation.

16. The apparatus according to claim 15, wherein the reflective surface is configured to reflect at least 10% of the ultraviolet radiation.

17. The apparatus according to claim 1, wherein the disinfection assembly comprises a heat source and the control circuitry is configured to activate the heat source to heat the disinfection chamber.

18. The apparatus according to claim 17, wherein the control circuitry is configured to activate the heat source to heat the disinfection chamber to a temperature of 40-300 degrees Celsius.

19. The apparatus according to claim 1, wherein the disinfection assembly comprises a disinfectant fluid assembly comprising a disinfectant fluid reservoir containing disinfectant fluid, and the control circuitry is configured to activate the disinfectant fluid assembly to release the disinfectant fluid from the disinfectant fluid reservoir into the disinfection chamber.

20. The apparatus according to claim 1, wherein the apparatus is packaged for commercial sale without the prefilled therapeutic substance reservoir.

\* \* \* \* \*